United States Patent [19]

Hölscher

[11] Patent Number: 4,732,662
[45] Date of Patent: Mar. 22, 1988

[54] MEASURING ELECTRODE

[75] Inventor: Uvo Hölscher, Stockelsdorf, Fed. Rep. of Germany

[73] Assignee: Drägerwerk Aktiengesellschaft, Lübeck, Fed. Rep. of Germany

[21] Appl. No.: 835,552

[22] Filed: Mar. 3, 1986

[30] Foreign Application Priority Data

Mar. 1, 1985 [DE] Fed. Rep. of Germany ....... 3507183

[51] Int. Cl.$^4$ ............................................. G01N 27/46
[52] U.S. Cl. ................................... 204/415; 204/291; 204/292; 204/403
[58] Field of Search ............... 204/1 P, 1 K, 1 T, 415, 204/400, 403, 291, 292

[56] References Cited

U.S. PATENT DOCUMENTS

| | | | |
|---|---|---|---|
| 2,672,441 | 3/1954 | White | 204/419 |
| 3,454,485 | 7/1969 | Hauk et al. | 204/415 |
| 3,462,353 | 8/1969 | Every et al. | 204/196 |
| 3,700,577 | 10/1972 | Grauer | 204/420 |
| 3,855,098 | 12/1974 | Fletcher | 204/420 |
| 4,119,498 | 10/1978 | Edwall et al. | 204/415 |
| 4,133,732 | 1/1979 | Boeke | 204/419 |
| 4,265,250 | 5/1981 | Parker | 204/415 |
| 4,273,134 | 6/1981 | Ricciardelli | 204/415 |
| 4,303,076 | 12/1981 | Danek | 204/415 |
| 4,333,473 | 6/1982 | Eberhard et al. | 204/415 |
| 4,400,258 | 8/1983 | Hans-Jurgen et al. | 204/415 |
| 4,401,547 | 8/1983 | Schinkmann et al. | 204/415 |
| 4,498,970 | 2/1985 | Chand | 204/415 |
| 4,536,274 | 8/1985 | Papadakis et al. | 204/415 |
| 4,599,157 | 7/1986 | Suzuki et al. | 204/415 |

FOREIGN PATENT DOCUMENTS

| | | |
|---|---|---|
| 0100988 | 2/1984 | European Pat. Off. ............ 204/435 |
| 0102033 | 3/1984 | European Pat. Off. . |
| 2121047 | 11/1971 | Fed. Rep. of Germany . |
| 2912834 | 9/1981 | Fed. Rep. of Germany . |

OTHER PUBLICATIONS

Yeung et al., "Low Impedance pH Sensitive Electrochemical Devices That are Potentially Applicable to Transcutaneous $P_{CO_2}$ Measurements", Acta Anaesth. Scan. 1978, Suppl. 68, pp. 137–141.

Primary Examiner—T. Tung
Attorney, Agent, or Firm—Walter Ottesen

[57] ABSTRACT

A measuring electrode is disclosed for pH measurement, in particular for the transcutaneous determination of $CO_2$ partial pressure. The measuring electrode is configured so that the shape thereof can be adapted to any shape of electrode carrier by mechanical working. For this purpose, the measuring electrode has a contact body containing the metal oxide in powdered form and the latter is in direct electrical contact with the metal of the metal oxide.

9 Claims, 2 Drawing Figures

MEASURING ELECTRODE

FIELD OF THE INVENTION

The invention relates to a metal and metal oxide measuring electrode for measuring pH and, in particular, for the transcutaneous determination of the $CO_2$ partial pressure.

BACKGROUND OF THE INVENTION

A metal and metal oxide measuring electrode of the above-mentioned kind is disclosed in published and examined German patent application DE-AS No. 21 21 047. In this electrode the metal is iridium, for example, and iridium oxide is the metal oxide; the part of the iridium electrode that is in contact with the fluid has a coating of iridium oxide. A method disclosed for producing this iridium oxide coating has three different steps for obtaining an oxide overlay that uniformly covers the iridium body.

From European patent application EP-PA No. 83108146.8, an electrochemical sensor for transcutaneous measurement of $CO_2$ partial pressure is known, which again uses a measuring electrode containing iridium and iridium oxide. In this electrochemical sensor, the sensitive measuring part of the measuring electrode includes an iridium wafer that is electroplated onto a carrier plunger and at least partially oxidized by electrochemical and/or thermochemical oxidation.

It is characteristic of both known measuring electrodes that chemical, electrochemical or physical methods are used to produce the oxide layer, and that the oxide layer is accordingly very thin. As a result, the shape of the electrode is determined by the carrier of the oxide layer. Because of this, it is no longer possible to effect subsequent mechanical treatment of the measuring electrode in order, for example, to adapt it to geometric conditions at the location where it is installed after it has been mounted in a measuring head, or to clean off dirt deposits. Instead, in the known measuring electrodes, care must be taken that under no circumstances will they undergo any mechanical change or damage whatsoever once the oxide layer has been applied.

SUMMARY OF THE INVENTION

It is an object of the invention to provide an improved metal and metal oxide measuring electrode of the above type such that the electrode body can be easily adapted to the shapes of the electrode carrier that are dictated by a particular measuring task, and that the labor-intensive manufacturing operations previously required for the precise assembly of the measuring electrode and measuring head can be avoided. Once the device has been assembled, it is possible to put the measuring surface into its final intended form on both the measuring electrode and the measuring head at the same time.

To attain this object, the invention provides that the measuring electrode has a contact body in which the metal oxide, which is in direct electrical contact with the metal of the metal oxide, is in powdered form.

The advantage of the measuring electrode according to the invention is that the contact body that is required for the measurement can be made in a separate operation, for instance from a sintered mixture of metal and metal oxide, and then applied to the electrode carrier. In its installed state, the contact body can be mechanically treated, and its outer form can be adapted to the shape of the measuring head, without damaging the measurement-sensitive metal/metallic oxide layer. Surprisingly, it has been found that a measuring electrode for pH measurement produced in this way reacts highly sensitively to changes in the pH values, which would not have been readily expected by one skilled in the art. All known measuring electrodes are made such that the very thin measurement-sensitive metal/metallic oxide boundary layer is exposed directly to the fluid that is to be tested. It was previously thought that distributing the measurement-sensing boundary layer within a matrix carrier would cause the measuring electrode to respond inadequately and slowly to changes in the pH value. Such matrix electrodes were therefore always used only as reference electrodes, for instance in the form of silver/silver chloride electrodes, which emit a constant reference signal of high accuracy for the measuring electrode. In this connection, reference may be made to DE-AS No. 29 12 834 and EP-PA No. 83107565.0, the latter also being referred to above.

The measuring electrode according to the invention is therefore suitable not only for measuring pH in fluids, but also and equally well for transcutaneous $CO_2$ measurement on the skin. It can be adapted to the particularly pronounced hemispherical embodiment of the measuring surface, and its response time is short enough for measuring pH in the electrolyte.

In a further feature of the invention, the metal oxide can be accommodated in a matrix carrier.

The matrix carrier having the metal oxide can advantageously be applied to an electric conductor made of the metal of the metal oxide, for instance in such a form that a metal wire is surrounded by a layer containing the metal oxide, the layer being for instance of polyvinyl chloride and acting as a matrix carrier.

It is suitable for the matrix carrier to contain both the metal oxide and its metal in powdered form, and for the electric conductor to be of any other desired metal, without generating a contact potential, which would interfere with the measurement, at the boundary surface between the metal oxide and the metal conductor.

In forming the measuring electrode, it proves to be particularly favorable to use a metal from the group of platinum metals; zirconium or titanium is also advantageous.

To make a hardenable contact body that can be adapted to the specialized shape of a given measuring electrode, a mixture ratio of approximately 45% by weight of metal, approximately 45% by weight of metal oxide, and approximately 10% by weight of matrix carrier has proved to be particularly suitable. The matrix carrier may suitably be made of polymerized plastic such as polyvinyl chloride or similar hardenable substances such as epoxy resin or silicon-containing organic substances such as silicon rubber, as well as ceramic or glass, and a hardenable adhesive binder can be added to these materials.

BRIEF DESCRIPTION OF THE DRAWING

The invention will now be described with reference to the drawing, wherein.

DESCRIPTION OF THE PREFERRED EMBODIMENTS OF THE INVENTION

Figure 1:
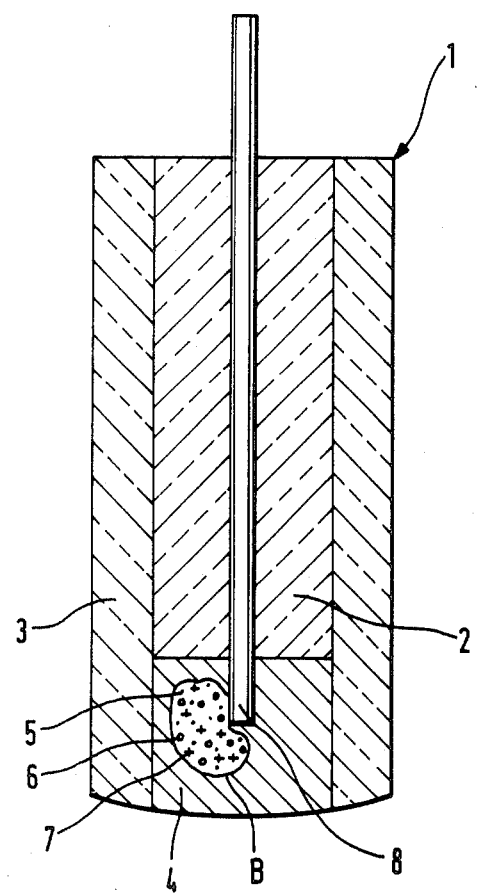
FIG. 1 is an elevation view, in section, of the measuring electrode according to the invention; and, FIG. 2 is an elevation view, in section, of a measuring head for transcutaneous $CO_2$ measurement according to the invention.

FIG. 1 shows a metal and metal oxide measuring electrode 1, which contains electrode carriers 2, 3 of acrylic glass; the electrode carrier 3 is arranged with respect to the electrode carrier 2 so as to leave a free space for the contact body 4. The contact body 4 includes a composition shown in detail in the area marked B. The composition contains the metal 5 represented by dots, the metal oxide 6 represented by small circles, and the matrix carrier 7 represented by crosses, in a fixed mixture ratio with one another. A metal conductor 8 for transmitting a signal to a measuring unit, not shown, is inserted into the contact body 4.

Figure 2:
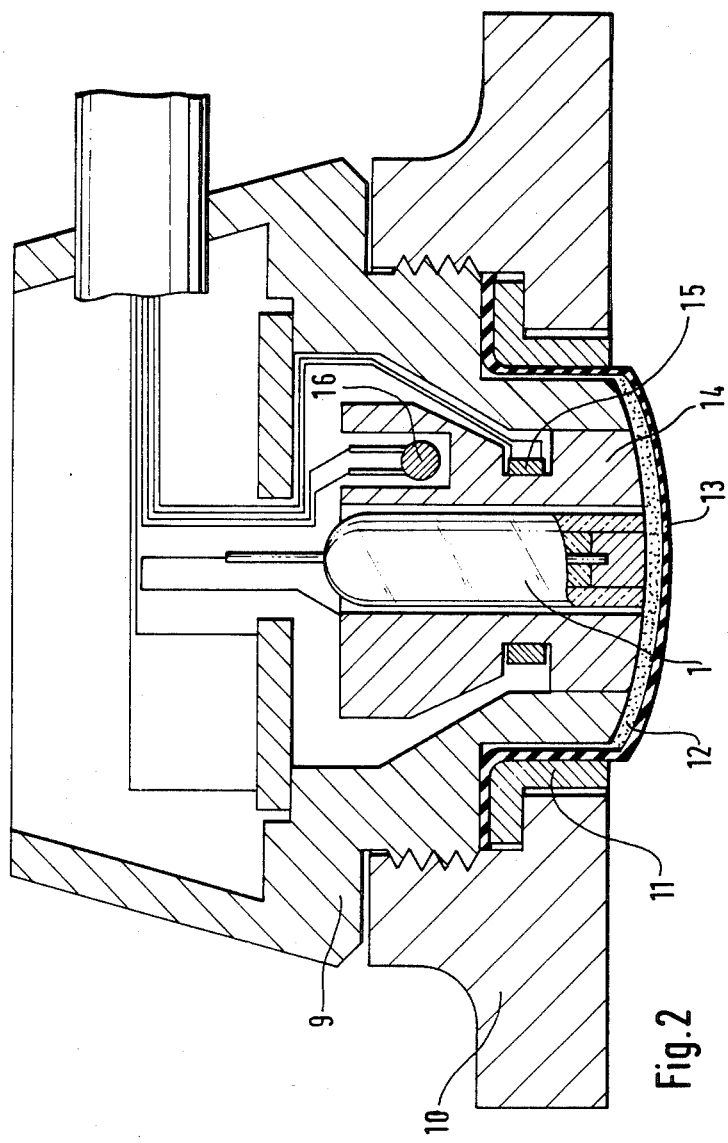

In the built-in state, shown in FIG. 2, the pH measuring electrode 1 is located in a measuring head 9 for transcutaneous measurement of the $CO_2$ partial pressure. The pH measuring electrode 1 is surrounded by a reference electrode 14 in a known manner. Heating means 15 keeps the two electrodes at a predetermined temperature, which is monitored by a thermistor 16. A securing ring 10, via a clamping ring 11, presses the membrane 13 against the measuring head 9 with the reference electrode 14 and the measuring electrode 1, thereby keeping the electrolyte 12 in close contact with the electrode surfaces and isolating it from the ambient.

When the pH measuring electrode 1 is installed in the measuring head 9, the measuring electrode 1 is first introduced into the space intended therefor inside the reference electrode 14, and then it can be machined together with the surfaces of the reference electrode 14 and measuring head 9 so that the surface of the measuring electrode 1 will be flush with the other surfaces. This process neither destroys nor impairs the boundary layer that actively participates in the measurement and that is located between the metal and the metal oxide inside the contact body 4.

It is understood that the foregoing description is that of the preferred embodiments of the invention and that various changes and modifications may be made thereto without departing from the spirit and scope of the invention as defined in the appended claims.

What is claimed is:

1. A measuring head assembly for making pH measurements such as for transcutaneously determining $CO_2$ partial pressure, the measuring head assembly comprising:

a measuring head defining a measuring head surface and having an opening formed in said surface;

a reference electrode having a first measuring surface and being mounted in said opening so as to cause said first measuring surface to be next to said measuring head surface, said reference electrode further having a receiving opening formed therein;

a measuring electrode unit mounted in said receiving opening, said unit including:

a supporting structure made of electrically insulating material and defining a cavity electrically insulated from said reference electrode;

an electrode lead seated in said supporting structure with a portion of said lead extending into said cavity;

a solid contact body filling said cavity so as to embed said portion of said lead therein to establish electrical contact therewith;

said solid contact body containing a mixture of a metal oxide, the metal of said oxide and a matrix carrier; and, said solid contact body having an outer surface defining a second measuring surface having a width greater than the diameter of said lead;

said measuring head surface, said first measuring surface and said second measuring surface being disposed one next to the other and being mechanically shaped so as to be flush and conjointly define a smooth, uninterrupted composite measuring surface.

2. The measuring head assembly of claim 1, said electrode lead being made of the same metal as said metal of said metal oxide.

3. The measuring head assembly of claim 1, said metal of said metal oxide being a platinum metal.

4. The measuring head assembly of claim 1, said metal of said metal oxide being a metal selected from the group consisting of zirconium and titanium.

5. The measuring head assembly of claim 1, said contact body comprising approximately 45% by weight of said metal, approximately 45% by weight of said metal oxide and approximately 10% by weight of said matrix carrier.

6. The measuring head assembly of claim 1, said matrix carrier being made of a polymerized plastic.

7. The measuring head assembly of claim 1, said matrix carrier being made of glass.

8. The measuring head assembly of claim 1, said matrix carrier being made of ceramic.

9. The measuring head assembly of claim 1, comprising: a membrane disposed adjacent said composite measuring surface; an electrolyte interposed between said composite measuring surface and said membrane; and, clamping means for clamping said membrane to said measuring head thereby keeping said electrolyte in close contact with said composite measuring surface.

* * * * *